United States Patent [19]

Athey et al.

[11] Patent Number: 5,726,341
[45] Date of Patent: Mar. 10, 1998

[54] AMINE NITRILE INTERMEDIATE FOR THE PREPARATION OF 2-HYDROXYETHYL IMINODIACETIC ACID

[75] Inventors: Phillip S. Athey; Druce K. Crump, both of Lake Jackson; David A. Wilson, Richwood, all of Tex.

[73] Assignee: The Dow Chemical Company, Midland, Mich.

[21] Appl. No.: 741,592

[22] Filed: Oct. 31, 1996

Related U.S. Application Data

[60] Provisional application No. 60/008,565, Dec. 13, 1995.

[51] Int. Cl.$^6$ ............................ C07C 255/18; C11D 3/26
[52] U.S. Cl. ........................ 558/441; 510/276; 510/313; 510/314; 510/332; 510/361
[58] Field of Search ............................ 558/441; 510/276, 510/313, 314, 332, 361

[56] References Cited

U.S. PATENT DOCUMENTS 3,864,378  2/1975  Homberg et al. .................... 260/465.5

OTHER PUBLICATIONS

Research Disclosure XP 000553648, Feb. 1996, No. 382, Emsworth, GB, Philip S. Athey et al.

International Search Report dated 21 Feb. 1997 issued by the EPO acting as the International Searching Authority in PCT/US96/17641.

*Primary Examiner*—Christine Skane
*Assistant Examiner*—Charles Boyer
*Attorney, Agent, or Firm*—Duane C. Ulmer

[57] ABSTRACT

A novel intermediate useful in the synthesis of 2-hydroxyethyl iminodiacetic acid is disclosed. The intermediate can be formed by contacting 2-hydroxyethyl amine with glycolonitrile to form an aminonitrile which can be hydrolyzed and contacted with additional glycolonitrile to form the nitrile intermediate which can be converted to 2-hydroxylethyl iminodiacetic acid via hydrolysis.

2 Claims, No Drawings

AMINE NITRILE INTERMEDIATE FOR THE PREPARATION OF 2-HYDROXYETHYL IMINODIACETIC ACID

This application claims benefit of U.S. Provisional Application No. 60/008,565 filed Dec. 13, 1995.

BACKGROUND OF THE INVENTION

The present invention is to novel intermediates useful in the synthesis of 2-hydroxyethyl iminodiacetic acid.

Chelants or chelating agents are compounds which form coordinate-covalent bonds with a metal ion to form chelates. Chelates are coordination compounds in which a central metal atom is bonded to two or more other atoms in at least one other molecule or ion, called a ligand, such that at least one heterocyclic ring is formed with the metal atom as part of each ring.

Chelating agents for metal ions, such as calcium, magnesium, iron, and manganese, are required for a wide range of technical fields. Examples of fields of application and end-uses are detergents, in electroplating, in water treatment, photography, textile industry, paper industry and also various uses in pharmaceuticals, cosmetics, foodstuffs and plant nutrition. Some of these activities may result in the chelating agents entering the environment. For example, agricultural uses or use in detergents may result in measurable quantities of the chelants in water.

As chelants may enter the environment from various uses, it is desirable to have chelants that would readily degrade after use. It would be particularly advantageous to have a chelant which is biodegradable, that is, susceptible to degradation by microbes which are generally naturally present in environments into which the chelants may be introduced.

Iminodiacetic acid derivatives are known to possess metal sequestering properties. U.S. Pat. No. 5,051,212 discloses that iminodiacetic acid, when combined with organic solvents, provide very good results in terms of soil removal from hard surfaces. The use of iminodiacetic acid derivatives in aqueous compositions for cleaning hard surfaces is reported in PCT Application No. WO 94/12606. The iminodiaetic acid derivatives in WO 94/12606 are also reported to have good biodegradable characteristics.

SUMMARY OF THE INVENTION

The present invention provides a novel composition of matter useful as an intermediate in the synthesis of 2-hydroxyethyl iminodiacetic acid (HEIDA). Specifically, the novel intermediate is a compound represented by the

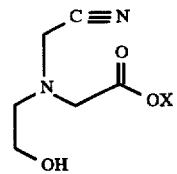

formula
wherein X represents hydrogen, an alkali metal or alkaline earth metal.

In another aspect, the invention is to a process for producing HEIDA by basic hydrolysis of the above-noted intermediate.

The present invention also relates to hard surface cleaning compositions containing HEIDA in an aqueous system. The hard surface cleaning compositions provide a method for cleaning hard surfaces comprising contacting a hard surface with a composition containing HEIDA and removing a portion of the composition from the hard surface.

DETAILED DESCRIPTION OF THE INVENTION

Starting materials for making the novel intermediate of the present invention include 2-hydroxyethylamine and glycolonitrile. A suitable reaction scheme for synthesis of the novel intermediate is shown in Scheme I. In step (a) 2-hydroxyethylamine is contacted with glycolonitrile to form N-cyanomethylamino-2-ethanol.

The molar ratio of 2-hydroxyethylamine to glycolonitrile is generally about 1:1 with a slight excess of glycolonitrile preferred.

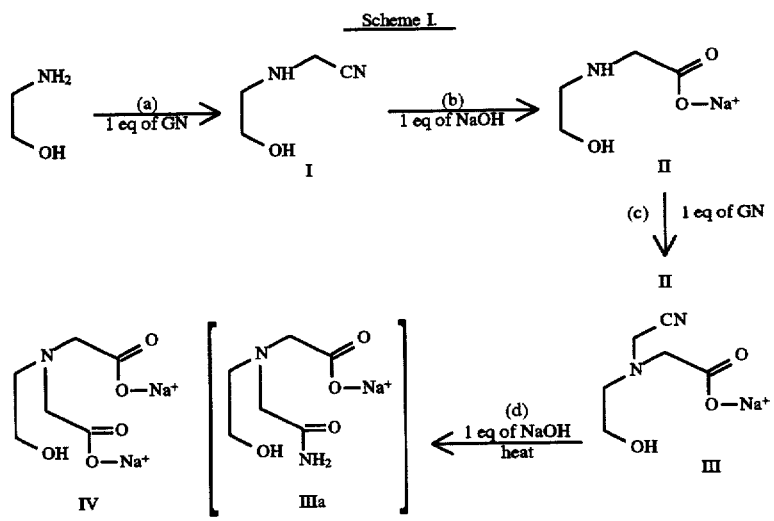

Scheme I

The hydrolysis of (I) with base gives N-carboxymethylamino-2-ethanol (II). Compound (II) is then reacted with additional glycolonitrile to form N-carboxymethyl-N-cyanomethylamino-2-ethanol (III). The molar ratio of (II) to glycolonitrile is generally about 1:1. In the above reactions, hydrogen cyanide and formaldehyde can be substituted for glycolonitrile.

Compound (III) is useful as an intermediate for the production of HEIDA. Specifically, compound (III) is hydrolyzed using a base such as sodium hydroxide to give the alkali metal salt of HEIDA. Hydrolysis of the nitrile group proceeds through the amide intermediate as depicted by structure IIIa in Scheme I on to the carboxymethyl group, and liberates ammonia which can be conveniently removed from the hydrolysis solution.

In Scheme I, the reaction is shown as occurring in the presence of aqueous sodium hydroxide. The above reactions may be carried out in the presence of other bases capable of hydrolyzing the nitrile functionality. Examples of other bases include alkali and alkaline earth metal hydroxides. Preferably sodium or potassium hydroxide are used in the above reaction scheme.

In addition to bases, the nitrile functionality can be hydrolyzed using strong acids such as hydrochloric or sulfuric acid. In this case, the ammonium salt of the respective acid is obtained as a by-product.

While reaction Scheme I shows the addition of one mole equivalent of base per mole of nitrile functionality, excess molar amounts of base can be used.

Preferably the glycolonitrile reaction steps (a) and (c) are carried out at a temperature from about 0° to about 100° C., preferably from about 15° to about 65° C. The hydrolysis of (I) and (1211) is generally done at a temperature from about 0° to about 120° C. Preferably the hydrolysis step (d) is done at a temperature from about 20° to about 105° C.

The hydrolysis of (III) to HEIDA results in a conversion in excess of 90 percent. Although Scheme I indicates that the production of III and HEIDA are done in step reactions, the production of IV can be accomplished by adding glycolonitrile to an alkaline solution of 2-hydroxyethylamine at a temperature to achieve alkaline hydrolysis. In this procedure, intermediate III is rapidly converted to IV.

HEIDA is a chelant which will biodegrade in both the semi-continuous activated sludge test (ASTM D-2667) and the modified Storm test (OECD 301B). In the activated sludge test, a standardized sludge containing municipal waste treatment plant organisms is used to biodegrade the chelant in the presence of metal ions representative of those found in the environment. Such a test simulates the environment encountered in a municipal waste treatment plant for screening the inherent biodegradability of non-volatile water-soluble compounds.

The modified Sturm test, in a similar manner contacts the chelant to a standardized culture of microorganisms. The evolution of carbon dioxide is used as a basis for determining microbial degradation when the test chelant is used as the sole carbon source.

HEIDA as a chelant is useful, for instance, in food products vulnerable to metal-catalyzed spoilage or discoloration; in cleaning and laundering products for removing metal ions, e.g. from hard water that may reduce the effectiveness, appearance, stability, rinsibility, bleaching effectiveness, germicidal effectiveness or other property of the cleaning agents; in personal care products like creams, lotions, deodorants and ointments to avoid metal-catalyzed oxidation and rancidity, turbidity, reduced shelf-like and the like; and in pulp and paper processing to enhance or maintain bleaching effectiveness. HEIDA can also be used in pipes, vessels, heat exchanges, evaporators, filters and the like to avoid or remove scaling; in pharmaceuticals; in metal working; in textile preparation, desizing, scouring, bleaching, dyeing and the like; in agriculture as in chelated micronutrients or herbicides; in polymerization or stabilization of polymers; in photography, e.g. in developers or bleaches; and in the oil field such as for drilling, production, recovery, hydrogen sulfide abatement and the like. The amount of chelating agent employed in the above noted applications are known in the art.

The use of HEIDA is particularly advantageous for use in cleaning compositions suitable for hard-surface cleaning, such as certain automatic dishwashing agents and kitchen or bathroom soil removal, especially calcium soap removal from bathtub surfaces. HEIDA is particularly advantageous for use in hard-surface cleaners for use in control of alkaline-earth metals, particularly calcium, and in preventing scaling. When used in hard-surface cleaners, HEIDA generally constitutes at least about 0.1 weight percent of the cleaner and typically less than about 25 percent. Preferably the hard-surface cleaner contains about 0.1 to about 15 percent HEIDA, and more preferably about 0.5 to about 5 percent.

In addition to being biodegradable, it has been found that HEIDA can be used in hard-surface cleaners free of organic solvents. This is particularly advantageous in that cleaning can be done without the concern for release of organic solvent into the environment.

Hard-surface cleaning compositions containing HEIDA are usually at an alkaline pH with a range of about 8 to about 14. Preferably the pH of the cleaning composition is from about 9 to about 13, and more preferably from about 10 to about 12.

In addition to HEIDA, hard surface cleaners of the present invention can optionally contain additional additives well known in the art. For example, surface-active agents, are beneficial in a hard-surface cleaner.

Such surface active agents include water-soluble surfactants such as synthetic anionic, nonionic, cationic, amphoteric and zwitterionic surfactants and mixtures thereof. Exemplary surfactants include the alkyl benzene sulfates and sulfonates, paraffin sulfonates, olefin sulfonates, alkoxylated (especially ethoxylated) alcohols and alkyl phenols, amine oxides, sulfonates of fatty acids and of fatty acid esters, and the like, which are known in the detergency art. Preferably, such surfactants contain an alkyl group in about the $C_{10}$–$C_{18}$ range. Anionic surfactants are commonly used in the form of their sodium, potassium or triethanolammonium salts. The nonionics advantageously contain from about 3 to about 17 ethylene oxide groups per mole of hydrophobic moiety. Representative cationic surfactants include quaternary ammonium compounds such as ditallow dimethyl ammonium chloride, and are preferably used in combination with nonionic surfactants. Preferred in the composition are about $C_{12}$–$C_{16}$ alkyl benzene sulfonates, about $C_{12}$–$C_{18}$ paraffin-sulfonates and the ethoxylated alcohols of the formula $RO(CH_2-CH_{2O})n$, with R being a $C_{12}$–$C_{15}$ alkyl chain and n being a number from 6 to 10, and the ethoxylated alcohol sulfates of formula $RO-(CH_2-CH_2O)n-SO_3M$, with R being a $C_{12}$–$C_{18}$ alkyl chain, is a number from about 2 to about 8, and M is H or an alkali metal ion.

Anionic surfactants are advantageously present at levels from about 0.3 percent to about 8 percent of the hard surface cleaning composition. Nonionic surfactants, are preferably used at levels between about 0.1 percent to about 6 percent by weight of the composition. Mixtures of surfactants are also useful.

Other optional ingredients include detergent builders, within the skill in the art, including nitrilotriacetate (NTA), polycarboxylates, citrates, water-soluble phosphates such as tri-polyphosphate and sodium ortho- and pyro-phosphates, silicates, ethylene diamine tetraacetate (EDTA), amino-polyphosphonates, phosphates and mixtures thereof.

Other optional additives for the hard surface cleaners include detergent hydrotropes. Exemplary hydrotropes include urea, monoethanolamine, diethanolamine, triethanolamine and the sodium, potassium, ammonium and alkanol ammonium salts of xylene-, toluene-, ethylbenzene- and isopropyl-benzene sulfonates.

The hard-surface cleaning compositions of the invention also optionally contain an abrasive material. The abrasive materials include water-insoluble, non-gritty materials known for their relatively mild abrasive properties. It is preferred that the abrasives used herein not be undesirably "scratchy". Abrasive materials having a Mohs hardness of no more than about 7 are preferred; while abrasives having a Mobs hardness of no more than about 3, are useful to avoid scratches on finishes such as aluminum or stainless steel. Suitable abrasives include inorganic materials, especially such materials as calcium carbonate and diatomaceous earth, as well as materials such as Fuller's earth, magnesium carbonate, China clay, actapulgite, calcium hydroxyapatite, calcium orthophosphate, dolomite and the like. The aforesaid inorganic materials can be described as "strong abrasives". Organic abrasives such as urea-formaldehyde, methyl methacrylate melamine-formaldehyde resins, polyethylene spheres and polyvinylchloride are advantageously used to avoid scratching on certain more delicate surfaces, such as plastic surfaces. Preferred abrasives have a particle size range of about 10–1000 microns and are preferably used at concentrations of about 5 percent to about 30 weight percent of the hard surface cleaning compositions.

Thickeners are preferably used to suspend the abrasives. Levels of thickener difficult to rinse from the cleaned surfaces are undesirable. Accordingly, the level is preferably less than about 2 percent, preferably from about 0.25 to about 1.5 percent. Exemplary thickeners include polyacrylates, xanthan gums, carboxymethyl celluloses, swellable smectite clay, and the like.

Soaps, especially soaps prepared from coconut oil fatty acids are also optionally included in the hard surface cleaners.

Optional components include components within the skill in the art to provide aesthetic or additional product performance benefits. Such components include perfumes, dyes, optical brighteners, soil suspending agents, detersive enzymes, gel-control agents, thickeners, freeze-thaw stabilizers, bactericides, preservatives, and the like.

The hard-surface cleaning compositions of the invention are advantageously in the form of liquid compositions, preferably aqueous compositions, including concentrates, containing as the essential ingredient HEIDA. Preferably a surfactant is also present, more preferably in a concentration that corresponds to from about 2 to about 6 percent surfactant. Concentrated liquid compositions preferably contain from about 6 to about 10 percent surfactant.

Alternatively, the compositions herein are in the form of creamy scouring cleansers, preferably containing an abrasive material, surface-active agent, and HEIDA.

The cleaning compositions can be packaged in a container that comprises a means for creating a spray, e.g., a pump, aerosol propellant or spray valve. The composition can be thus conveniently applied to the surface to be cleaned by conventional means, such as wiping with a paper towel or cloth, without the need for rinsing.

All parts, percentages and ratios herein are by weight unless otherwise indicated.

The invention will be further clarified by a consideration of the following examples which are intended to be purely exemplary of the present invention.

EXAMPLES

Example 1

The stepwise procedure for the synthesis of the nitrile precursor to HEIDA:

Synthesis of (I): In a 50 mL round bottom flask was placed 2.0 g (0.033 mol) of 2-hydroxyethylamine, 30 mL of water and a magnetic stir bar. While the solution was stirring the glycolonitrile (40% GN, aqueous solution, 4.67 g, 0.033 mole) was added dropwise. The solution was stirred at room temperature for 2 h. A $^{13}$C NMR indicated that the reaction was complete. $^{13}$C NMR (D$_2$O): $\delta$39.0, 52.3, 62.9, 121.6 ppm.

Synthesis of (II): The contents of the solution were carried onto the hydrolysis step without purification by the addition of 2.62 g of 50% NaOH. After stirring at room temperature for 3 h the hydrolysis was complete. The solution was brought to a boil to liberate the ammonia. The heating was continued until no further ammonia was detected. $^{13}$C NMR (D$_2$O): $\delta$ 52.7, 54.9, 63.3, 182.5 ppm.

Synthesis of (III): To the solution of II, which was at room temperature, was added the glycolonitrile (GN, 40% aqueous, 4.62 g, 0.033 mole) dropwise. After stirring for 30 min at room temperature the $^{13}$C NMR indicated that the reaction was complete. The nitrilo intermediate was carried onto the next step without further purification. $^{13}$C NMR (D$_2$O): $\delta$ 45.5, 58.5, 60.8, 61.4, 119.5, 180.5 ppm.

Hydrolysis of (III) to (IV): To the aqueous solution of III was added 2.62 g of 50% NaOH. After stirring at room temperature for 3 h the hydrolysis was complete. The solution was brought to a boil to liberate the ammonia. The heating was continued until no further ammonia was detected. $^{13}$C NMR (D$_2$O): $\delta$59.7, 61.6, 62.2, 182.7 ppm.

Example 2

The procedure of ASTM D2667 is used to determine the inherent biodegradablity of HEIDA (IV).

Copper titration value is used to measure the extent of biodegradation of the chelating agents during the procedure. Titration is performed using ammonium purpurate (indicator for complexometric titration, commercially available from Aldrich Chemical Co., Inc. under the trade designation Murexide) as the indicator at approximately pH 8, and using sodium acetate as buffer. Titration of 2.0 mg HEIDA (0.0105 moles) in 100 mL water with 0.01 molar copper chloride gives an endpoint of 1.06 mL, representing a 1:1 chelation of copper. Analysis is performed daily for a period of 28 days.

Results of the biodegradation screening are given in Table I:

TABLE I

| Compound | Time for greater than 80% loss of chelation |
|---|---|
| NTA (std.) | 3 days |
| HEIDA | 5 days |
| EDTA (std.) | greater than 28 days |

A control is used to verify the absence of interfering chelating substances in the test.

The results of the biodegradability test show that HEIDA is inherently biodegradable and could be expected to be utilized by organisms in a municipal treatment facility after an acceptable acclamation period.

Example 3

Calcium chelation capacity of HEIDA

The applicability of HEIDA for use in hard surface cleaners, is measured by the calcium oxalate and calcium carbonate titrations.

For titration with calcium oxalate, between 1 to 2 millimoles of HEIDA is weighed in a 60 mL beaker. After the addition of 30 mL deionized water and 5 mL of a 3% ammonium oxalate solution, the pH is slowly brought to about 10 by the addition of 20% sodium hydroxide while stirring. The pH is then adjusted to about 11.6 within sodium hydroxide and the solution is titrated with 0.1 m $CaCl_2$ to the first permanent turbidity. The chelation valve is then determined from the mL of titrant used based on the following calculation.

$$\text{Chelation Value} = \frac{(\text{mL titrant used} \times \text{molarity titrant}) \times 100 \text{ mg } CaCO_3 \text{ per mmole}}{\text{sample wt. in grams} \times \text{activity of sample (as acid form)}}$$

The chelation value is the mg of $CaCO_3$ that can be chelated by one active gram of a chelant, such as HEIDA.

For the carbonate titration, the above procedure is duplicated with 2 mL of 20% sodium carbonate solution replacing the use of the ammonium oxalate solution.

The turbidity produced in the carbonate titration is due to the formation of calcium carbonate, while the turbidity produced in the oxalate titration is due to calcium oxalate. The results for the titration of HEIDA in the presence of oxalate and carbonate is compared with iminodiacetic acid (IDA) and given in Tables II and III respectively.

TABLE II

OXALATE TITRATION

| Chelant | Chelation Value |
|---------|-----------------|
| IDA     | 1               |
| 2-HEIDA | 206             |

TABLE III

CARBONATE TITRATION

| Chelant | Chelation Value |
|---------|-----------------|
| IDA     | 5               |
| 2-HEIDA | 425             |

The results from both the oxalate and carbonate titrations show that HEIDA exhibits a chelation value far superior to IDA, depending on the indicator used. Therefore, for applications requiring calcium control, such as in hard surface cleaners, HEIDA can be used as a more biodegradable substitute for EDTA.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A compound represented by the following formula:

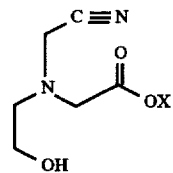

wherein X is hydrogen or an alkali or alkaline earth metal.

2. A process for producing 2-hydroxyethyl iminodiacetic acid comprising hydrolyzing an aqueous solution of a compound of the formula:

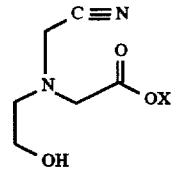

with an acid or base to produce 2-hydroxyethyl iminodiacetic acid wherein X is hydrogen or an alkali or alkaline-earth metal.

* * * * *